(12) United States Patent
Barnes et al.

(10) Patent No.: US 6,586,625 B1
(45) Date of Patent: Jul. 1, 2003

(54) SYNTHESIS OF 2-HALOBENZYL ALKANOIC ACID

(75) Inventors: Hamlin H. Barnes, Fort Collins, CO (US); Fredric R. Askham, Loveland, CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 09/566,953

(22) Filed: May 8, 2000

(51) Int. Cl.⁷ .................................. C07C 63/33

(52) U.S. Cl. ...................... 562/493; 562/496

(58) Field of Search ................... 562/493, 496

(56) References Cited

U.S. PATENT DOCUMENTS 5,789,634 A * 8/1998 Sullivan et al.

\* cited by examiner

*Primary Examiner*—Alan L. Rotman
*Assistant Examiner*—Hector M Reyes
(74) *Attorney, Agent, or Firm*—Edward S. Irons

(57) ABSTRACT

A method for synthesizing compounds of Formula I

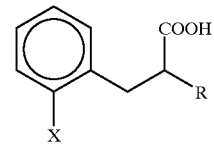

in which R is alkyl or aryl and X is any halogen is described.

5 Claims, No Drawings

SYNTHESIS OF 2-HALOBENZYL ALKANOIC ACID

FIELD OF THE INVENTION

This invention relates to an improved synthesis of 2-halobenzylalkanoic acid compounds of Formula I:

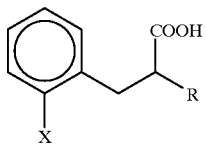

in which R is alkyl or aryl, and X is any halogen.

BACKGROUND OF THE INVENTION

U.S. Pat. No. 5,789,634 describes a synthesis of 2-substituted, 7-haloindenes and the conversion thereof to bridged metallocenes useful as olefin polymerization catalysts. Two methods for the synthesis of 2-substituted, 7-haloindenes are illustrated by Examples 1 and 2 of that patent. The labor intensive Example 1 method requires five steps.

Example 2 of U.S. Pat. No. 5,789,634 describes a synthesis of 2-ethyl-7-chloroindene from a 2-halobenzyl halide intermediate. To provide the intermediate, lithium diisopropylamide in heptane/THF/ethylbenzene was added to a sodium butanoate/THF slurry. 2-chlorobenzyl chloride was added to the slurry after it had been stirred at ambient temperature for 24 hours. The reaction was quenched by water addition, and the resultant aqueous layer was separated and neutralized. 2-(2-chlorobenzyl)butanoic acid was concentrated in the organic layer. Synthesis of 2-ethyl-7-chloroindene from the 2-(2-chlorobenzyl)butanoic acid provided a 33% overall yield of 2-ethyl-7-chloroindene.

SUMMARY OF THE INVENTION

Pursuant to this invention, overall yields of Formula I compounds in excess of 80% isolated yield may be achieved in two steps. In preferred embodiments, R in the Formula I compounds is $C_1$ to $C_{14}$ aryl or $C_1$ to $C_{20}$ alkyl. The substituted halobenzylalkanoic acids so produced are readily converted in good yield to 2-substituted, 7-haloindenes.

DETAILED DESCRIPTION OF THE INVENTION

Pursuant to this invention, an alkanoate metal salt/diisopropylamide reaction mixture is added to a 2-halobenzyl halide reactant to provide Formula I compound yields which may be in excess of 80%.

According to this invention Formula I compounds are synthesized by:

(i) providing a slurry of an alkali metal salt of an acid of Formula II (R-COOH), wherein X is any halogen and R is $C_6$ to $C_{14}$ aryl or $C_6$ to $C_{20}$ alkyl or $C_1$ to $C_{14}$ aryl in a non-interfering solvent;

(ii) combining said step (i) alkali metal salt solution with a solution of a non-nucleophilic strong base, preferably an alkali metal dialkyl amide in a non-interfering solvent, wherein a first reaction mixture is formed and wherein said first reaction mixture is typically a slurry;

(iii) providing a solution of a 2-halobenzyl halide in a non-interfering solvent; and (iv) adding said step (ii) reaction mixture to said step (iii) 2-halobenzyl halide solution, wherein a second reaction mixture combining a Formula I compound is produced.

In step (i), any alkali metal salt of a Formula II acid may be used. Sodium butanoate is preferred. Suitable non-interfering solvents are $C_5$ to $C_{10}$ alkanes and cycloalkanes. Cyclohexane is preferred. Preferably, the relative proportions of Formula II acid salt and non-interfering solvent are from about 5 wt% to 30 wt% acid-salt in the solution.

Any alkali metal salt of a non-nucleophilic strong base may be used. Typical strong bases include $C_1$ to $C_{10}$ dialkyl amides. Lithium diisopropyl amide is preferred. Alkali metal salts of hexaalkyldisilazide, e.g.,

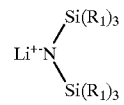

in which each R, may be the same or a different $C_1$ to $C_{10}$ alkyl group may be used.

The alkali metal dialkyl amide is preferably utilized in a mixed solvent, e.g., THF-cyclohexane medium. The proportions of alkali metal salt of a non-nucleophilic strong base, e.g., lithium diisopropyl amide and solvent are selected to provide a reaction mixture containing at least about 5 to 20 wt % of a Formula I compound.

The 2-halo-2-substituted indene may be obtained by further reaction of the resulting Formula I compound in known manner, for example, by following the procedures described in U.S. Pat. No. 5,789,634.

Example 1

Synthesis of 2-(2-Chlorobenzyl)-Isovaleric Acid (1) The sodium salt of the isovaleric acid was prepared by addition of 8 mol acid to NaH (8.08 mol) in 4 L hexane and 576 g THF (8 mol, 1 equivalent). A slurry resulted. Be careful of $H_2$ venting.

Next 8.16 mol LDA-THF/1.5 M (cyclohexane) was added, and stirred overnight. A 12 L flask was used.

(2) The slurry, being quite thick, was added to 8.16 mol 2-chlorobenzyl chloride in 6 L hexane. Since all the reaction was a slurry, the reaction proceeded slowly, but whereas in previous experiments no exotherm was observed, this time a strong exotherm occurred, and cooling was used to maintain a temperature of 10–20° C. in the reaction flask. Stir out overnight.

We claim:

1. A method for synthesizing a compound of Formula I:

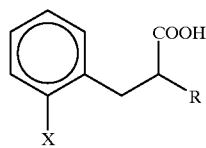

which comprises:

(i) providing a first reactant comprising salt of an acid of Formula II (R-COOH), wherein X is any halogen and R is $C_6$ to $C_{14}$ aryl or $C_6$ to $C_{20}$ alkyl in a non-interfering solvent;

(ii) combining said step (i) first reactant with a second reactant comprising an alkali metal salt of a non-nucleophilic strong base and a non-interfering solvent which may be the same as or different from said first reaction mixture non-interfering solvent, wherein a step (ii) reaction mixture is provided;

(iii) providing a solution of 2-halobenzyl halide in a non-interfering solvent which may be the same as or different from said step (i) or step (ii) non-interfering solvents; and (iv) adding said step (ii) first reaction mixture to said step (iii) 2-halobenzyl halide solution, wherein a step (iv) reaction mixture-containing a Formula I compound is produced.

2. The claim 1 method wherein said step (ii) alkali metal salt of a non-nucleophilic strong base is an alkali metal salt of a dialkyl amide or an alkali metal salt of a hexaalkyldisilazide.

3. The claim 1 or claim 2 method wherein said step (ii) alkali metal salt is a lithium salt.

4. The claim 1 method wherein each non-interfering solvent is a $C_6$ to $C_{10}$ alkane or cyclohexane.

5. A method which comprises:
(i) providing a solution in a non-interfering solvent of an acid of Formula II R-COOH, wherein R is $C_1$ to $C_{10}$ alkyl;

(ii) combining said step (i) solution with a solution of lithium diisopropyl amide in hexane, wherein a step (ii) reaction mixture is produced;

(iii) combining said step (ii) reaction mixture with a solution of 2-chlorobenzyl chloride in hexane, wherein a step (iii) reaction mixture containing a Formula I compound is produced.

* * * * *